US011918575B2

(12) United States Patent
Andries et al.

(10) Patent No.: US 11,918,575 B2
(45) Date of Patent: Mar. 5, 2024

(54) PZA AND CYTOCHROME BC1 INHIBITOR COMBINATION TREATMENT

(71) Applicant: Janssen Sciences Ireland Unlimited Company, County Cork (IE)

(72) Inventors: Koenraad Jozef Lodewijk Marcel Andries, Beerse (BE); Anil Koul, Edegem (BE); Maria Cristina Villellas Arilla, Turnhout (BE)

(73) Assignee: Janssen Sciences Ireland Unlimited Company, County Cork (IE)

( * ) Notice: Subject to any disclaimer, the term of this patent is extended or adjusted under 35 U.S.C. 154(b) by 71 days.

(21) Appl. No.: 17/540,299

(22) Filed: Dec. 2, 2021

(65) Prior Publication Data
US 2022/0088012 A1    Mar. 24, 2022

Related U.S. Application Data

(62) Division of application No. 16/490,677, filed as application No. PCT/EP2018/054860 on Feb. 28, 2018, now Pat. No. 11,224,596.

(30) Foreign Application Priority Data

Mar. 1, 2017 (EP) .................................. 17158607

(51) Int. Cl.
*A61K 31/4965* (2006.01)
*A61K 31/438* (2006.01)
*A61K 31/4545* (2006.01)
*A61K 31/47* (2006.01)
*A61K 31/498* (2006.01)
*A61P 31/06* (2006.01)

(52) U.S. Cl.
CPC ........ *A61K 31/4965* (2013.01); *A61K 31/438* (2013.01); *A61K 31/4545* (2013.01); *A61K 31/47* (2013.01); *A61K 31/498* (2013.01); *A61P 31/06* (2018.01)

(58) Field of Classification Search
CPC .................................................. A61K 31/4965
See application file for complete search history.

(56) References Cited

U.S. PATENT DOCUMENTS

| 6,090,820 | A  | 7/2000  | Barbachyn et al. |
| 8,304,419 | B2 | 11/2012 | Chong et al. |
| 9,029,389 | B2 | 5/2015  | No et al. |
| 10,155,756 | B2 | 12/2018 | Lu et al. |
| 2011/0183342 | A1 | 7/2011  | Lewinsohn et al. |
| 2014/0073622 | A1 | 3/2014  | Soneda et al. |
| 2016/0318925 | A1 | 11/2016 | Miller et al. |
| 2017/0313697 | A1 | 11/2017 | Lu et al. |

FOREIGN PATENT DOCUMENTS

| JP | 2011046745 | 3/2011 |
| KR | 1999/008399 | 1/1999 |
| KR | 2014/0011017 | 1/2014 |
| KR | 2014/0065902 | 5/2014 |
| KR | 2015/0060224 | 6/2015 |
| MA | 27360 | 6/2005 |
| WO | WO 1996/15130 | 5/1996 |
| WO | WO 2004/011436 | 2/2004 |
| WO | WO 2005/012292 | 2/2005 |
| WO | WO 2008/082490 | 7/2008 |
| WO | WO 2009/120789 | 10/2009 |
| WO | WO 2010/078408 | 8/2010 |
| WO | WO 2011/057145 | 5/2011 |
| WO | WO 2011/113606 | 9/2011 |
| WO | WO 2012/143796 | 10/2012 |
| WO | WO 2013/033070 | 3/2013 |
| WO | WO 2013/033116 | 3/2013 |
| WO | WO 2013/033167 | 3/2013 |
| WO | WO 2013/127269 | 9/2013 |
| WO | WO 2014/015167 | 1/2014 |
| WO | WO 2015/014993 | 2/2015 |
| WO | WO 2016/062151 | 4/2016 |
| WO | WO 2016/073524 | 5/2016 |
| WO | WO 2017/001660 | 1/2017 |
| WO | WO 2017/001661 | 1/2017 |
| WO | WO 2017/216281 | 12/2017 |
| WO | WO 2017/216283 | 12/2017 |
| WO | WO 2018/158280 | 9/2018 |

OTHER PUBLICATIONS

Product Details for ANDA 081319, approval date Jun. 30, 1992, available at https://www.accessdata.fda.gov/scripts/cder/ob/results_product.cfm?Appl_Type=A&Appl_No=081319#28287.*
Product Details for NDA 050705, approval date May 31, 1994, available at https://www.accessdata.fda.gov/scripts/cder/ob/results_product.cfm?Appl_Type=N&Appl_No=050705#5550.*
Zhang et al., Mechanisms of Pyrazinamide Action and Resistance, Microbiol Spectr. 2013; 2(4): 1-12, Published online Aug. 27, 2013.*
Pethe et al., Discovery of Q203, a potent clinical candidate for the treatment of tuberculosis, Nat Med. Sep. 2013;19(9):1157-60. doi: 10.1038/nm.3262. Epub Aug. 4, 2013.*
International Search Report for PCT/EP2016/065499 dated Sep. 9, 2016.
International Search Report for PCT/EP2016/065503 dated Aug. 12, 2016.
International Search Report for PCT/EP2017/064652 dated Jul. 21, 2017.
International Search Report for PCT/EP2017/064654 dated Jul. 21, 2017.
International Search Report for PCT/EP2018/054860 dated May 28, 2018.

(Continued)

*Primary Examiner* — Svetlana M Ivanova
(74) *Attorney, Agent, or Firm* — Sofia Kopelevich

(57) ABSTRACT

The present invention relates to novel combinations, which are useful in the treatment of tuberculosis.

6 Claims, 1 Drawing Sheet

(56) References Cited

OTHER PUBLICATIONS

Bundegaard, H. "Design of Prodrugs" p. 1-92, Elesevier, New York—Oxford (1985).
Cihan-Üstündag et al, Molecular Diversity, 2012, vol. 16 (3), pp. 525-539.
Database Registry Chemical Abstract Service, RN 1783117-90-7; Jun. 18, 2015, XP 055221200.
Database Registry Chemical Abstract Service, RN 1156922-31-4; Jun. 14, 2009, XP055221197.
Database Registry Chemical Abstract Service, RN 1409441-72-0; Dec. 2, 2012, XP 055221191.
Database Registry Chemical Abstract Service, RN 1638404-01-9; Dec. 10, 2014, XP055221179.
Database Registry Chemical Abstract Service, RN 1394533-85-7; Sep. 18, 2012, XP 055221174.
Database Registry Chemical Abstract Service, RN 1638474-30-2; Dec. 11, 2014, XP055221208.
Güzel et al, General Papers Arkivoc 2006, xii, pp. 98-110.
Kang et al., J. Medicinal Chemistry, 2014, 57 (12), pp. 5293-5305.
Moraski et al, ACS Medicinal, Chemistry Letters, vol. 4, No. 7, pp. 675-679, 2013.
Moraski et al, ACS Infectious, Diseases, vol. 1, No. 2, pp. 85-90, 2015.
Ollinger et al, Plos One, vol. 8, No. 4, pp. e60531, 2013.
Pethe et al "Discovery of Q203, a potent clinical candidate for the treatment of tuberculosis", Nature Medicine, 19, 1157-1160 (2013).
Tang et al, ACS Medicinal Chemistry, Letters. vol. 6, No. 7, pp. 814-818, 2015.
Tester, R. et al., Bioorganic and Medicinal Chemistry Letters 20 (2010) 2560-2563.
Tiwari et al., ACS Med Chem Lett, 2014, vol. 5, pp. 587-591.
CAS Registry No. 1831341-34-4; STN entry date: Dec. 17, 2015; 2H-Pyrazolo[4,3-c]pyridine-3-carboxamide, N-[[4-(cyclohexylmethylamino)phenyl methyl]-4,5,6,7-tetrahydro-, hydrochloride (1:1).
Chetty et al., "Recent advancements in the development of anti-tuberculosis drugs", Bioorganic & Medicinal Chemistry Letters, Pergamon, Amsterdam, NL, vol. 27, No. 3, Nov. 29, 2016 (Nov. 29, 2016), pp. 370-386.
Gualano G et al, Infectious Disease Reports, 2016, vol. 8 (2), pp. 43-49.
Lamprecht D et al, Nature Communications, vol. 7 (1), pp. 1-14, Aug. 10, 2016.
Zhang et al, Microbiological Spectrum, Mechanisms of Pyrazinamide Action and Resistance, vol. 2 issue 4, pp. 1-12, 2013.
Zumla A et al, The Lancet Respiratory Medicine, 2015, vol. 3(3), pp. 220-234.
Clain et al., "Novel Treatments for Drug-Resistant Tuberculosis", Clinical Medicine Insights, Therapeutics, vol. 8, pp. 21-28, 2016.
CAS1831341-33-3, STN entry date: Dec. 17, 2015; N-(4-(cyclohexyl(methyl)amino)benzyl)-4,5,6,7-tetrahydro-2H-pyrazolo[4,3-c]pyridine-3-carboxamide.
CAS1625238-97-2, STN entry date: Sep. 24, 2014; N-(4-(cyclohexyl(methyl)amino)benzyl)-2-methylpyrazolo[1,5-a]pyrimidine-3-carboxamide.
CAS1320875-52-2, STN entry date: Aug. 21, 2011; N-(4-(cyclohexyl(methyl)amino)benzyl)-5,7-dimethylpyrazolo[1,5-a]pyrimidine-3-carboxamide.
CAS1278717-74-0, STN entry date: Apr. 13, 2011; N-(4-(cyclohexyl(methyl)amino)benzyl)-2,5,7-trimethylpyrazolo[1,5-a]pyrimidine-3-carboxamide.
CAS1289433-56-2, STN entry date: May 3, 2011; N-(4-(cyclohexyl(methyl)amino)benzyl)-3,6-dimethyl-4-oxo-3,4-dihydrofuro[2,3-d]pyrimidine-5-carboxamide.
CAS1299681-23-4, STN entry date: May 24, 2011; N-(4-(cyclohexyl(methyl)amino)benzyl)-6-methyl-4-oxo-1,4-dihydrofuro[2,3-d]pyrimidine-5-carboxamide.

* cited by examiner

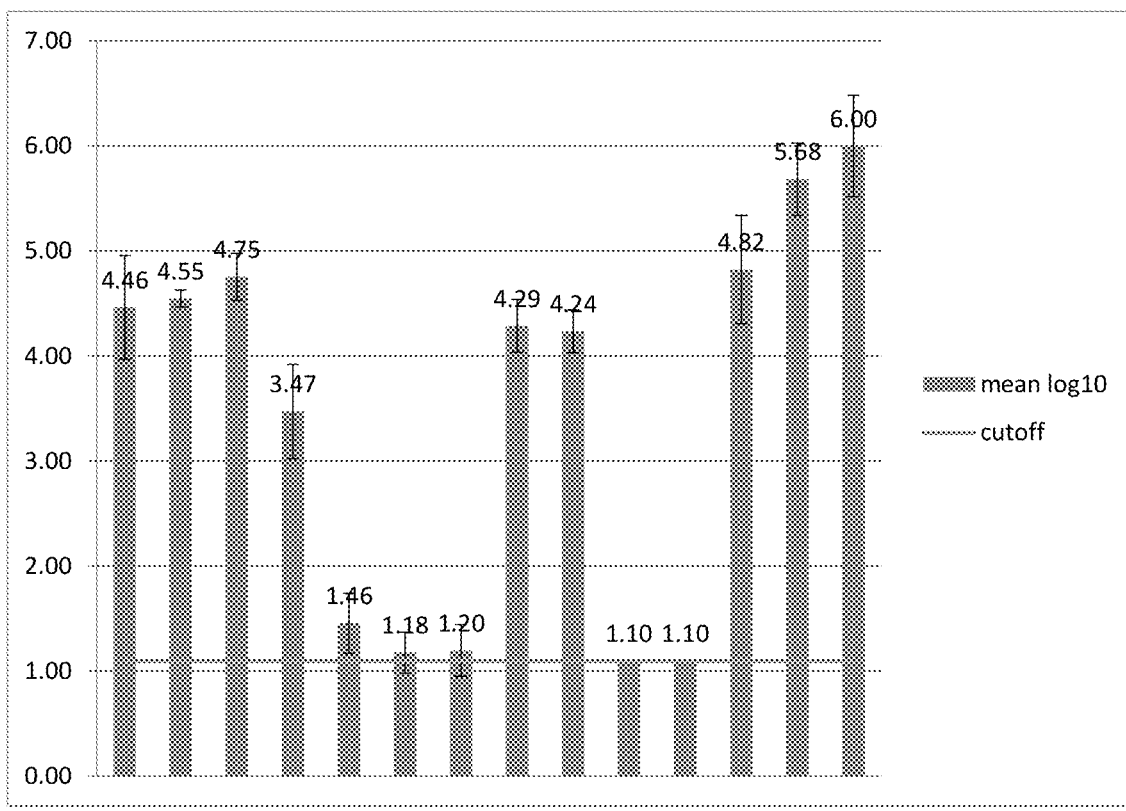

PZA AND CYTOCHROME BC1 INHIBITOR COMBINATION TREATMENT

CROSS REFERENCE TO RELATED APPLICATIONS

This application is a divisional of U.S. application Ser. No. 16/490,677, filed Sep. 3, 2019, which is a national stage of PCT Application No. PCT/EP2018/054860, filed Feb. 28, 2018, which claims priority from European Patent Application No. 17158607.6, filed Mar. 1, 2017, the entire disclosures of which are hereby incorporated by reference in their entirety.

The present invention relates to novel combinations. The invention also relates to such combinations for use as pharmaceuticals, for instance in the treatment of bacterial diseases, including diseases caused by pathogenic mycobacteria such as *Mycobacterium tuberculosis*. Such combinations may be advantageous in the treatment of tuberculosis.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs or new combinations of drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become non-infectious. The 4- to 6-month continuation, or sterilizing, phase is required to eliminate persisting bacilli and to minimize the risk of relapse. Novel drugs or combinations that potentially shorten treatment to 2 months or less would be extremely beneficial. It would also be beneficial to reduce the number of drugs required. Facilitating compliance by requiring less intensive supervision may also be beneficial. Obviously, novel drugs or novel combinations of drugs that reduce both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for new therapies (e.g. combinations) likely to demonstrate activity against drug-resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fueled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients, the only prophylactic treatment available for latent TB is two three-months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response cause death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is pathophysiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection.

Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new therapies to treat bacterial infections, especially mycobacterial infections.

As mentioned above, several drugs already exist for the treatment of tuberculosis, for instance, pyrazinamide (often abbreviated to PZA). This drug is known to be bacteriostatic, but is also bacteriocidal on actively replicating tuberculosis bacteria. It is not used as a single agent, but commonly used in combination with isoniazid and rifampicin for the treatment of tuberculosis.

There are several other known drugs that are used for treating tuberculosis, which may act via different mechanisms of action. For instance, Journal article *Nature Medicine*, 19, 1157-1160 (2013) by Pethe et al "Discovery of Q203, a potent clinical candidate for the treatment of tuberculosis" identifies a specific compound that was tested against *M. tuberculosis*. This compound Q203 is depicted below.

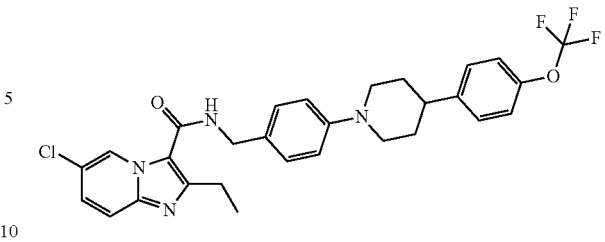

It is postulated that it acts by interfering with ATP synthase in *M. tuberculosis*, and that the inhibition of cytochrome $bc_1$ activity is the primary mode of action. Cytochrome $bc_1$ is an essential component of the electron transport chain required for ATP synthesis.

This clinical candidate is also discussed in journal article, *J. Medicinal Chemistry*, 2014, 57 (12), pp 5293-5305. It is stated to have activity against MDR tuberculosis, and have activity against the strain *M. tuberculosis* H37Rv at a $MIC_{50}$ of 0.28 nM inside macrophages. Positive control data (using known anti-TB compounds bedaquiline, isoniazid and moxifloxacin) are also reported. This document also suggests the mode of action, based on studies with mutants. It appeared that Q203 was highly active against both replicating and non-replicating bacteria.

Further documents relating to the Q203 and analogues include patent documents WO 2011/113606 and WO 2015/014993. International patent application WO 2012/143796 discloses various compounds for use in the treatment of inflammation.

Other documents disclosing compounds that may be useful in the inhibition of cytochrome $bc_1$ activity include international patent applications WO 2017/001660 and WO 2017/001661, the disclosures of which are hereby incorporated by reference.

As mentioned above, combinations of tuberculosis drugs are also known, with certain combinations being recommended for use by the WHO. Combination therapies are described in several documents including WO 2015/107482, which discloses combinations of tuberculosis drugs including specifically a macrocyclic molecule, which is tested in combination with: rifampicin and/or ethambutol; amoxicillin and/or ethionamide; and isoniazid and/or rifampicin. This document also discloses that the macrocycle can be combined with a number of other drugs, including pyrazinamide or Q203, amongst a list of possible tuberculosis drugs. Some journal articles also disclose various combinations of tuberculosis drugs, for example *Nature Communications*, Lamprecht and co., 2016, 7, 12393, which tests amongst other things, Q203 in combination with other tuberculosis drugs such as clofazamine and bedaquiline.

It is of great benefit to be able to discover new combinations and/or better combinations of known drugs given that: —combinations are likely to remain the treatment guidelines (e.g. given drug-resistant bacterial forms); and —access to the best combinations will ultimately advance patient outcomes.

SUMMARY OF THE INVENTION

It has been found that certain combinations, for use in the treatment of tuberculosis, have been found to be particularly effective (as described hereinafter in the biological results). Such combinations were found to be synergistic and are therefore encompassed within the scope of the invention. In general, it was seen that combining pyrazinamide (PZA) and a cyctochrome $bc_1$ inhibitor (e.g. Q203, as defined above, or another, as described herein) led to extremely potent activities in killing *Mycobacterium tuberculosis*.

Thus, in an aspect of the invention, there is provided:
a combination comprising:
(i) PZA, or a pharmaceutically acceptable salt thereof; and
(ii) a cytochrome $bc_1$ inhibitor, or a pharmaceutically acceptable salt thereof,
which combination may be referred to as "combination of the invention".

Given the results seen with a combination of PZA and a cytochrome $bc_1$ inhibitor, in terms of potent activity, there is also provided:
a combination consisting of (e.g. consisting essentially of) the following active ingredients:
(i) PZA, or a pharmaceutically acceptable salt thereof; and
(ii) a cytochrome $bc_1$ inhibitor, or a pharmaceutically acceptable salt thereof,
which combination may also be referred to as "combination of the invention".

Such combinations of the invention are useful as medicaments. For instance, such combinations may in particular be useful in the treatment of a mycobacterial infection (especially *Mycobacterium tuberculosis*, which may also be referred to as "tuberculosis" herein). For the purposes of the invention, tuberculosis means any form of tuberculosis such as the active form or the latent form. The latent (or dormant) for is elaborated upon hereinafter. The form may also include a drug-resistant form of tuberculosis (e.g. a mutidrug resistant form, MDR form, which includes an extensively multi-drug resistant form). The combinations of the invention may be expected to be effective against MDR tuberculosis given that MDR refers to resistance due to a bacterium resistant to at least isoniazid and rifampicin (with or without resistance to other drugs), and hence pyrazinamide (PZA) and Q203 (as an example of a cytochrome $bc_1$ inhibitor), and therefore the combinations of the invention, may still therefore be useful in the treatment of MDR tuberculosis.

However, although it is thought that two drugs of this combination may themselves be sufficient (e.g. potent enough), such combinations of the invention may further comprise additional antibacterial (e.g. anti-tuberculosis) drugs. For instance, any one or more (e.g. one or two) of the following antibacterial (e.g. anti-tuberculosis) agents (or pharmaceutically acceptable salts thereof) may be mentioned in addition to the essential two agents (so forming e.g. a triple or quadruple combination, etc):
other antibacterial agents known to interfere with the respiratory chain of *Mycobacterium tuberculosis*, including for example direct inhibitors of the ATP synthase (e.g. bedaquiline, e.g. bedaquiline fumarate, or any other compounds that may have be disclosed in the prior art), inhibitors of ndh2 (e.g. clofazimine);
other antibacterial agents that may target the electon transport chain, e.g. that target the cytochrome bd oxidase (e.g. Aurachin D analogues);
other mycobacterial agents for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; delamanid; quinolones/fluoroquinolones (such as for example moxifloxacin, gatifloxacin, ofloxacin, ciprofloxacin, sparfloxacin); macrolides (such as for example clarithromycin, amoxycillin with clavulanic acid); rifamycins; rifabutin; rifapentin; as well as others, which are currently being developed (but may not yet be on the market; see e.g. http://www.newtbdrugs.org/pipeline.php), for instance delanamid, pretonamid and the like.

A cytochrome $bc_1$ inhibitor is referred to herein, and may more specifically be referred to as a compound that inhibits cytochrome $bc_1$ in the ETC of *Mycobacterium tuberculosis*, thereby interfering with ATP synthesis resulting in preventing the bacterium from replicating, or killing it. In an embodiment, the cytochrome $bc_1$ inhibition of such a compound is its primary mode of action (against *Mycobacterium tuberculosis*). By "inhibits" in this context, we mean that the compound is indicated as inhibiting (cytochrome $bc_1$) or is known to inhibit, e.g. in a relevant test or assay, for instance as described hereinafter. For example, the compound may be tested for anti-bacterial activity in any one of Pharmacological Tests 1 to 4 described hereinbelow and, in an embodiment, is understood to fall within the scope of "inhibitor" in this context if anti-bacterial activity is measured, for instance, if the $IC_{50}$ value is less than 10 μM (or if the $pIC_{50}$ value is more than 5). In order to definitively determine whether a compound is a cytochrome $bc_1$ inhibitor (acting primarily via that mode of action), generation of mutants resistant to the compound and further sequencing of the whole genome may be performed as was performed in the *Nature Medicine* journal article referenced herein (i.e. journal article *Nature Medicine*, 19, 1157-1160 (2013) by Pethe et al, the content of which is hereby incorporated by reference, in particular the detail provided around identifying a compound as being a cytochrome $bc_1$ inhibitor). For instance, $MIC_{50}$ values may be tested against mutant strains of *Mycobaterium* tuberculosis. Where mutants show an increase in $MIC_{50}$ for the compound being tested (e.g. an increase of several orders of magnitude, such as 10-fold or 50-fold or, in an embodiment, 100-fold higher or more) but remain susceptible to other or standard anti-tuberculosis drugs, then the compound is a "$bc_1$ inhibitor" when the mutation is at the cytochrome b subunit (qcrB, also known as Rv2196 of the cytochrome $bc_1$ complex). Sequence analysis (e.g. of qcrB) may also confirm that mutation of Thr313 to either alanine or isoleucine is associated with resistance to the tested compound, thereby also confirming that the tested compound is a "$bc_1$ inhibitor". Further still, a re-introduction of mutation Ala313 by homologous recombination in parental *Mycobacterium tuberculosis* H37Rv may be tested to see if it confers resistance to the compound being tested, which may further demonstrate that the substitution is directly and specifically involved in the mechanism of resistance, also further confirming that the tested compound is a "$bc_1$ inhibitor". Any compound targeting the respiratory chain may potentially inhibit the production of ATP—and hence a cytochrome $bc_1$ inhibitor may also interfere with ATP synthesis, for instance causing a reduction in ATP levels (e.g. intracellular ATP). Hence, a suitable test may be conducted that measures intracellular ATP levels (to determine whether the test compound reduces ATP levels) and (a) further test(s) can be conducted thereafter to determine e.g. whether the relevant compound targets ATP synthase (e.g. bedaquiline is an ATP synthase inhibitor) or a cytochrome $bc_1$ inhibitor, for instance conducting the mutation tests as specified above.

Currently, there is no enzymatic assay test for a "$bc_1$ inhibitor", and the reason for this is that the bcc complex (more information around which can be found at https://ncbi.nlm.nih.gov/pmc/articles/PMC4205543/) is suggested to interact directly with other enzymes (to achieve electron transfer) and functions as a supercomplex.

In an embodiment, particular bc$_1$ inhibitors that may be mentioned include: Q203 (e.g. in a non-salt form);

any of the compounds disclosed in international patent applications WO 2011/113606 and WO 2015/014993, the contents of both of which are hereby incorporated by reference;

any of the compounds disclosed in international patent applications WO 2017/001660 and WO 2017/001661, the contents of both of which are hereby incorporated by reference.

For instance, the cytochrome bc$_1$ inhibitor may be a compound of the following general formula (I):

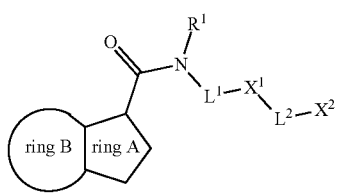

(I)

for example, wherein:
ring A is a 5-membered aromatic ring containing one or more (e.g. one or two) heteroatom(s) (e.g. nitrogen);
ring B is a 6-membered aromatic ring containing one or more (e.g. one or two) heteroatom(s) (e.g. nitrogen);
ring A and ring B together form a 6,5-fused aromatic bicycle containing one to four (e.g. 2 or 3) heteroatoms (e.g. nitrogen atoms);
ring A and ring B are optionally substituted by one or more substituents selected from $X^a$;
$L^1$ represents an optional linker group —C($R^a$)($R^b$)—;
$R^a$ and $R^b$ independently represents H or $C_{1-3}$ alkyl, or are linked together to form a 3- to 5-membered carbocyclic ring;
$X^1$ represents an aromatic linker group optionally substituted by one or more substituents selected from $X^b$;
$L^2$ represents a nitrogen containing linker ring (e.g. a monocyclic ring, bicyclic ring or spiro ring for instance as described herein) optionally substituted by one or more substituents selected from $X^c$;
$X^2$ represents —S(O)$_2$—$Y^1$, —C(O)—$Y^2$, —$Y^3$ or —O—$Y^4$;
$Y^3$ and $Y^4$ independently represent halo (e.g. fluoro; e.g. in the case of $Y^3$ only), $C_{1-6}$ alkyl (optionally substituted by one or more fluoro atoms; e.g. in the case of $Y^3$ may form a vinylic group, i.e. =C directly attached, and optionally further substituted) or an aromatic group optionally substituted by one or more substituents selected from $X^d$;
$Y^1$ and $Y^2$ independently represent $C_{1-6}$ alkyl (optionally substituted by one or more fluoro atoms) or an aromatic group (optionally substituted by one or more substituents selected from $X^e$);
$X^a$, $X^b$, $X^c$, $X^d$ and $X^e$ independently represent one or more independent substituents selected from halo (e.g. chloro or fluoro), —CN, $C_{1-6}$ alkyl (optionally substituted by one or more substituents selected from fluoro and —O$C_{1-3}$ alkyl, in which the latter alkyl group may itself be optionally substituted by one or more fluoro atoms) and —O$C_{1-6}$ alkyl (optionally substituted by one or more fluoro atoms). For the avoidance of doubt, when there is more than one $X^a$ to $X^e$ substituent present (e.g. two $X^b$ substituents on the $X^1$ moiety), then those $X^b$ substituents may be the same or different.

In an embodiment, the compound of formula (I) may be one in which:
when $X^2$ represents —S(O)$_2$—$Y^1$ or —C(O)—$Y^2$, then such a group is attached to a heteroatom (e.g. nitrogen atom) of the $L^2$ nitrogen-containing linker group (examples of which $L^2$ group may be described below).

In an embodiment, the compound of formula (I) may be one in which:
$L^1$ is not present; or
$L^1$ represents —CH$_2$—.

In an embodiment, the compound of formula (I) represents one in which:
$R^a$ and $R^b$ independently represent H or $C_{1-3}$ alkyl (and, in an embodiment, represent H).

In an embodiment, the compound of formula (I) may be one in which:
the $X^1$ aromatic linker group represents phenyl, napthyl or a bicyclic 6,6- or 6,5-fused heteraryl group (containing one to three, e.g. one or two, heteroatoms);
the $X^1$ aromatic linker group represents either a carbocyclic (e.g. phenylene, naphthylene) or heterocyclic (e.g. a bicyclic 6,6- or 6,5-fused) linker, hence may represent the following moieties (where the first squiggly line represents the point of attachment to the $L^1$ radial):

-phenylene- (especially a 1,4-phenylene), e.g.:

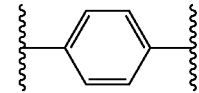

-naphthylene, e.g.:

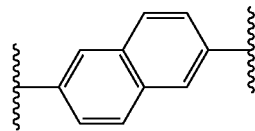

-quinolylene (such as 2-quinolylene), e.g.:

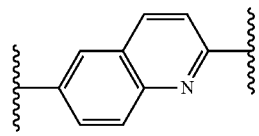 [SMILES: *c1ccc2nc(*)ccc2c1]

-quinoxalinyl (such as 2-quinolylene), e.g.:

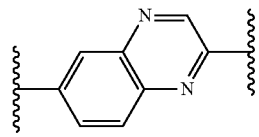 [SMILES: *c1ccc2nc(*)cnc2c1]

in an embodiment, the $X^1$ moiety represents a carbocyclic aromatic linker group (for instance a phenylene or naphthylene, e.g. as depicted above); and/or in an embodiment, the $X^1$ aromatic linker group is not substituted (by possible $X^b$ substituents).

In an embodiment, the compound of formula (I) may be one in which:

the $L^2$ nitrogen-containing linker group is a 3- to 8-membered (e.g. 4- to 6-membered) nitrogen-containing ring, e.g. in which the nitrogen atom is directly linked to $X^1$, and in which that nitrogen ring may form a part of a further cycle (e.g. a further 3- to 8- or 4- to 6-membered ring), so forming e.g. a spiro-cycle or a fused cycle;

the following $L^2$ groups may specifically be mentioned herein (where the upper squiggly line represents the point of attachment to $X^1$ and the lower squiggly line represents the point of attachment to $X^2$):

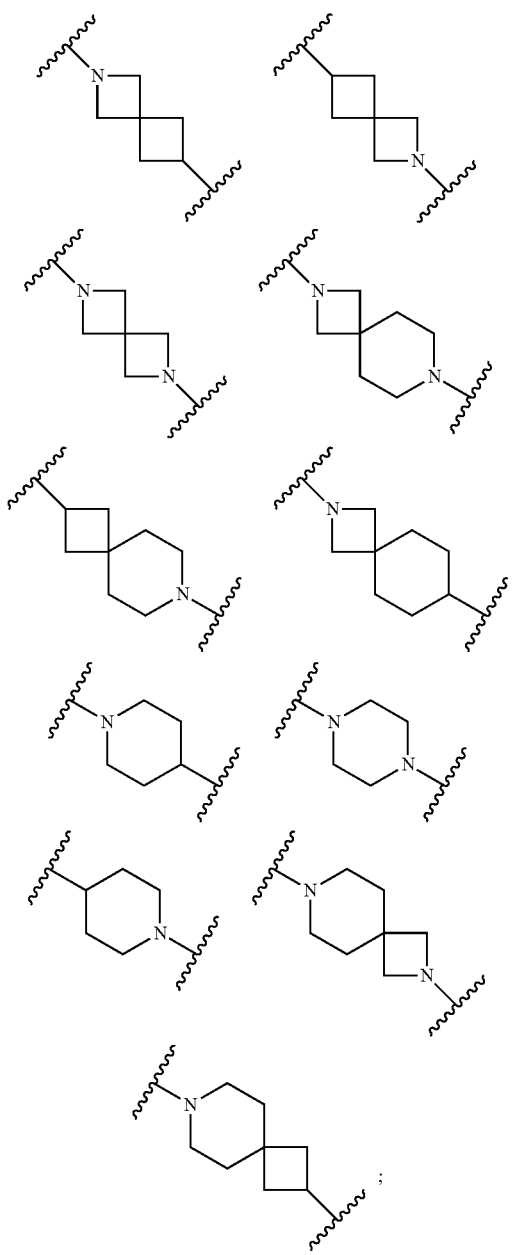

and/or the $L^2$ nitrogen-containing linker group (or ring) is not substituted (by one or more substituents selected from X').

In an embodiment, the compound of formula (I) represents one in which:

$X^2$ represents $-Y^3$ or $-O-Y^4$;

$Y^3$ and $Y^4$ independently represent an aromatic group that is phenyl, napthyl or a bicyclic 6,6- or 6,5-fused heteraryl group (containing one to three, e.g. one or two, heteroatoms), all of which are optionally substituted as defined herein (for example, $Y^3$ and $Y^4$ may represent phenyl, optionally substituted, e.g. in the para-position, by $X^d$);

$X^d$ represents one or more (e.g. one) substituent(s) selected from $C_{1-3}$ alkyl and $-OC_{1-3}$alkyl (both of which latter alkyl moieties are themselves optionally substituted by one or more fluoro atoms, so forming for example a $-CF_3$ or $-OCF_3$ substituent).

In an embodiment, the compound of formula (I) represents one in which:

$X^2$ represents $-S(O)_2-Y^1$ or $-C(O)-Y^2$; and in an aspect, $Y^1$ and $Y^2$ independently represent $C_{1-6}$ (e.g. $C_{1-3}$) alkyl optionally substituted by one or more fluoro atoms (so forming e.g. a $-CF_3$ group); or in another aspect, $Y^1$ and $Y^2$ independently represent an aromatic group (e.g. a carbocylic aromatic group) optionally substituted as defined herein (for instance, $Y^1$ and $Y^2$ may represent phenyl optionally substituted by one or more $X^e$ substituents; in which $X^e$ may represent $C_{1-3}$ alkyl or $-O-C_{1-3}$ alkyl, which alkyl moieties are themselves optionally substituted by one or more fluoro atoms, so forming e.g. a $-CF_3$ group).

In particular, the compound of formula I may contain the following bicycle defined by ring A and ring B:

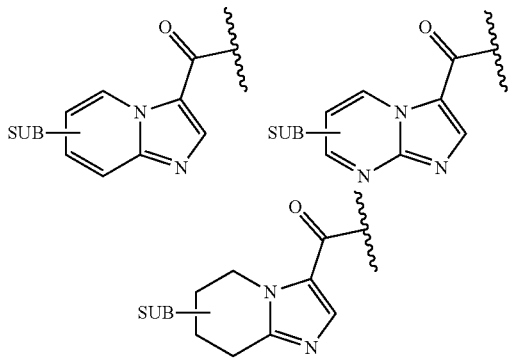

wherein "SUB" represents one or more substituent(s) (as defined herein) each located at any one of the available positions of either ring of the bicycle; and in an embodiment, the ring A and ring B together represent the first structure depicted (the imidazopyridine).

In particular, the cytochrome $bc_1$ inhibitor is a specific compound as defined herein.

BRIEF DESCRIPTION OF THE FIGURE

FIG. 1 shows the Measurement of CFUs in 14 study groups after the end of treatment, as described hereinafter (11 study groups comprise treatment regimes comprising BDQ, Q203, PZA, Cpd X or various combinations of the foregoing, and 3 study groups are control groups; for more detail see examples hereinbelow).

DETAILED DESCRIPTION OF THE INVENTION

Active ingredients (e.g. the essential PZA and cytochrome $bc_1$ inhibitor, and/or the optional further antibacterial agents)

of the combinations of the invention may also be in the form of a pharmaceutically acceptable salt. Pharmaceutically-acceptable salts include acid addition salts and base addition salts. Such salts may be formed by conventional means, for example by reaction of a free acid or a free base form of the relevant active ingredient (e.g. PZA, cytochrome $bc_1$ inhibitor or other optional antibacterial agent) with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable acid addition salts as mentioned hereinabove are meant to comprise the therapeutically active non-toxic acid addition salt forms that the relevant active ingredient (e.g. PZA, cytochrome $bc_1$ inhibitor or other optional antibacterial agent) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicyclic, pamoic and the like acids.

For the purposes of this invention solvates, prodrugs, N-oxides and stereoisomers of the relevant active ingredient (e.g. PZA, cytochrome $bc_1$ inhibitor or other optional antibacterial agent) are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds mentioned herein (e.g. of formula (I)) may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds mentioned herein (e.g. of formula (I)) wherein a hydroxyl, amino, sulfhydryl, carboxy or carbonyl group in that compound is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of formula (I) may contain double bonds and may thus exist as E (entgegen) and Z (zusammen) geometric isomers about each individual double bond. Positional isomers may also be embraced by the compounds of formula (I). All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of formula (I) may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of formula (I) may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the formula (I).

In the structures shown herein, where the stereochemistry of any particular chiral atom is not specified, then all stereoisomers are contemplated and included as the compounds of formula (I). Where stereochemistry is specified by a solid wedge or dashed line representing a particular configuration, then that stereoisomer is so specified and defined.

The compounds of formula (I) may exist in unsolvated as well as solvated forms with pharmaceutically acceptable solvents such as water, ethanol, and the like, and it is intended that both solvated and unsolvated forms are embraced.

The compounds of formula (I) also embrace isotopically-labeled compounds which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of formula (I). Exemplary isotopes that can be incorporated into compounds of formula (I) include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of formula (I) (e.g., those labeled with $^3H$ and $^{14}C$) are useful in compound and for substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of formula (I) can generally be prepared by following procedures analogous to those disclosed in the description/Examples hereinbelow, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

The term "halo", when used herein, preferably includes fluoro, chloro, bromo and iodo.

Aromatic groups may be aryl or heteroaryl. Where it is specified that aromatic groups are carbocyclic, such groups may also be referred to as "aryl". Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydro-naphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring. Most preferred aryl groups that may be mentioned herein are "phenyl".

Aromatic heterocyclic groups may also be referred to as "heteroaryl" groups, and when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. It is also preferred that each of the individual rings, when the heteroaryl is polycyclic, are aromatic. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group. Most preferred heteroaryl groups that may be mentioned herein are 5- or 6-membered aromatic groups containing 1, 2 or 3 heteroatoms (e.g. preferably selected from nitrogen, oxygen and sulfur).

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

When "aromatic" groups are referred to herein, they may be aryl or heteroaryl. When "aromatic linker groups" are referred to herein, they may be aryl or heteroaryl, as defined herein, are monocyclic (or, in another embodiment, polycyclic) and attached to the remainder of the molecule via any possible atoms of that linker group. However, when, specifically carbocyclic aromatic linker groups are referred to, then such aromatic groups may not contain a heteroatom, i.e. they may be aryl (but not heteroaryl).

For the avoidance of doubt, where it is stated herein that a group may be substituted by one or more substituents (e.g. selected from $C_{1-6}$ alkyl), then those substituents (e.g. alkyl groups) are independent of one another. That is, such groups may be substituted with the same substituent (e.g. same alkyl substituent) or different (e.g. alkyl) substituents.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of formula (I) that are the subject of this invention include those that are stable. That is, compounds of formula (I) include those that are sufficiently robust to survive isolation from e.g. a reaction mixture to a useful degree of purity.

The combinations of the invention may be useful in the treatment of active tuberculosis and may also be useful in the treatment of latent or dormant tuberculosis. The combinations may be effective by having a bacteriostatic effect, but may also have a bacteriocidal effect. It is indicated that they may also be useful in the treatment of latent tuberculosis because the combinations (or any one of the essential components of the combination, e.g. the $bc_1$ inhibitor, such as Q203) may act by interfering with ATP synthase, which may also impact on the latent tuberculosis bacilli. It is an advantage to have combinations that are effective against active tuberculosis and also against latent tuberculosis, for instance that can have an impact on or kill latent tuberculosis bacilli. In order to control the tuberculosis epidemic, this is important as the latent tuberculosis can get reactivated to cause active tuberculosis, and several factors can influence this happening, e.g. suppression of host immunity by use of immunosuppressive agents (such as antibodies against tumour necrosis factor α or interferon-γ). Doses of the combination (and each active ingredient of the combination) may be influenced if it is being used to treat active or latent tuberculosis.

The quantity of each drug should be an effective amount to elicit a biological or medicinal response. The daily dose of the drug may of course vary depending on factors such as: —already approved (e.g. by an appropriate regulatory body such as EMA or the US FDA) recommended daily doses; —efficacy of doses lower than those already approved (or being studied in clinical trials); —patient tolerability; —the daily dose of the other drug (or drugs) forming part of the relevant combination; —any synergistic effects between the components of the combination; —the mode of administration.

Regarding doses, in general, satisfactory results will be obtained when the relevant compound of the combination of the invention is administered at a daily dosage not exceeding 1 or 2 grams, e.g. in the range from 1 to 50 mg/kg or from 10 to 50 mg/kg body weight. However, doses may be adjusted depending on response rates.

Daily doses for PZA (or a pharmaceutically acceptable salt thereof) may, for instance, be 15 to 30 mg/kg (up to 2 g), or, an alternative dosing regimen of 50 to 75 mg/kg (up to 3 g) twice a week. Hence, daily doses may be between for instance 500 mg and 2000 mg (e.g. about 1000, about 1500 or about 2000 mg).

Daily doses for the cytochrome $bc_1$ inhibitor (e.g. Q203, or a pharmaceutically acceptable salt thereof) may, for instance be 1.5 to 15 mg/kg (up to 1 g). Hence daily doses may for instance be between 50 mg and 1000 mg and, in one embodiment, may be between 50 mg and 250 mg (e.g. about 50, 75, 100, 150 or 200 mg) or in another embodiment may be between 50 mg and 800 mg (e.g. between 100 mg and 800 mg, for instance about 100, 200, 300, 400, 500, 600, 700 or 800 mg).

Optional further antibacterial drugs that may be included in the combinations of the invention may be administered at daily doses recommended by a regulatory body (when e.g. approved in combination with other antibacterial agents), and are preferably administered at a daily dosage not exceeding 1 or 2 grams, e.g. in the range from 1 to 50 mg/kg body weight (for instance, in the range from 1 to 25 mg/kg, from 1.5 to 25 mg/kg, or from 2 to 15 mg/kg body weight).

Given that combinations of the invention are seen to be advantageous (e.g. synergistic, as exemplified in the examples section), then such combinations are envisioned to have, in one embodiment, a possible advantage that fewer (or no) other antibacterial (anti-tuberculosis) drugs are required in the treatment phase, and/or, in another embodiment, a possible advantage that the doses (e.g. daily doses) of either one of the two essential components of the combination (PZA or the cytochrome $bc_1$ inhibitor) and/or any additional optional antibacterial agent (as defined herein) may be less than expected (for example, less than may be recommended by a regulatory body, when labelled for use in combination with other antibacterials such as rifampin/isoniazid and/or ethambutol, or less than that tested in clinical trials). Hence, the expected daily doses of PZA, or a pharmaceutically acceptable salt thereof, may be 7.5 to 15 mg/kg (up to 1 g). Hence, daily doses may be between for instance 250 mg and 1000 mg (e.g. about 250, 500, about 750 or about 1000 mg). And the expected daily doses of the cytochrome $bc_1$ inhibitor (e.g. Q203, or a pharmaceutically acceptable salt thereof) may be 0.75 to 7.5 mg/kg (up to 500 mg). Hence daily doses may for instance be between 25 mg and 500 mg and, in an embodiment, may be between 25 mg and 125 mg (e.g. about 25, 50, 75 or 100 mg).

All amounts mentioned in this disclosure refer to the free form (i.e. non-salt form). The values given below represent free-form equivalents, i.e., quantities as if the free form would be administered. If salts are administered the amounts need to be calculated in function of the molecular weight ratio between the salt and the free form.

The doses (e.g. daily doses) described herein are calculated for an average body weight specified, and should be recalculated in case of paediatric applications, or when used with patients with a substantially diverging body weight.

The treatment duration for tuberculosis can be more than a year. However, it is envisioned that treatment duration may be reduced using the combinations of the invention. For instance, treatment duration may be 36 weeks or less, for instance 24 weeks or less. In certain embodiments, the treatment duration may be less than 20 weeks, for instance 16 weeks or less, or, 12 weeks or less.

In aspects of the invention, there is provided combinations of the invention, as described herein, for use as medicaments or pharmaceuticals. Such combinations may be useful in the treatment of a disease caused by *Mycobacterial tuberculosis* (e.g. in the treatment of tuberculosis).

Hence, there is also provided a pharmaceutical composition (or formulation) comprising a pharmaceutically acceptable carrier and, as active ingredient, a therapeutically effective amount of a combination of the invention. Such combinations may be formulated into pharmaceutical compositions as described hereinafter.

Accordingly, in another aspect of the invention, there is provided a method of treating a patient suffering from, or at risk of, a disease caused by *Mycobacterial tuberculosis* (tuberculosis), which method comprises administering a therapeutically effective amount of a combination of the invention or a pharmaceutical composition of the invention. In an embodiment, the patient is human.

In further embodiments, there is provided a method of treatment as defined herein wherein the method further comprises a treatment duration period as defined herein (e.g. a treatment duration of 36 weeks or less, 24 weeks or less or, in a particular embodiment, a treatment period of 16 weeks or less or 12 weeks or less). Alternatively, there is provided a combination for use as described herein, wherein the use is for a certain duration period (e.g. a treatment duration of 36 weeks or less, 24 weeks or less or, in a particular embodiment, a treatment period of 16 weeks or less or 12 weeks or less).

The components or antibacterial drugs of the combinations of the invention (including the two essential antibacterial drugs of the combination and the further optional drugs) may be formulated separately (e.g. as defined herein) or may be formulated together so forming for example a fixed dose formulation. The latter may have advantages in terms of compliance. In some embodiments, the two (or optionally more) antibacterial drugs of the combinations of the invention can be co-administered, in other embodiments the antibacterial drugs (of the combinations) may be sequentially administered, while in still other embodiments they can be administered substantially simultaneously. In some of the latter embodiments, administration entails taking such antibacterial drugs within 30 minutes or less of each other, in some embodiments 15 minutes or less of each other. In some embodiments, the antibacterial drugs are administered once per day, at approximately the same time each day. For example, the antibacterial drugs are administered within a time range of 4 hours of the original time of administration on the first day, that is, ±2 hours, or ±1 hour, or in still other embodiments ±30 minutes of the time on the original administration day.

In some embodiments, the antibacterial drugs of the invention are administered as separate oral capsules or oral tablets. Other formulations may include solid dispersions.

Hence, when a combination is referred to herein, such a combination may be a single formulation comprising all antibacterial drugs of the combinations of the invention (i.e. the two essential ones mentioned herein and, optionally, one or more further antibacterials) or it may be a combination product (such a kit of parts) where each of the antibacterial drugs of the combinations of the invention may be packaged together either as separate forms (each comprising one of the antibacterial drugs) or as two or more forms (depending on the total number of antibacterial drugs in the combination of the invention). In an embodiment, each antibacterial drug of the combination of the invention is formulated separately and/or is also packaged separately but may be labelled for use in combination with one or more of the other antibacterial drugs of the combinations of the invention. The antibacterial drugs of the combination (as described herein) may be co-administered, sequentially administered, or administered substantially simultaneously. Hence the individual dosage forms of each of the antibacterial drugs can be administered as separate forms (e.g., as separate tablets or capsules) as described herein or, in other embodiments, may be administered as a single form containing all three active substances or as two forms (one containing any two of the active substances and the other containing the remaining active substance).

The antibacterial drugs of the combinations of the invention may be formulated into various pharmaceutical forms for administration purposes. As mentioned herein, this formulating may be done on an individual antibacterial drug or a combination of antibacterial drugs that form part of the combinations of the invention. As appropriate, compositions may include those usually employed for systemically administering drugs. To prepare the pharmaceutical compositions the relevant antibacterial drug (or combination of relevant antibacterial drugs) is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

Any pharmaceutical composition mentioned herein (e.g. a pharmaceutical composition comprising one antibacterial drug or a combination of antibacterial drugs of the combination of the invention) may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

As mentioned herein, the combination of antibacterial drugs as described herein may be co-administered, sequentially administered, or administered substantially simultaneously (as described herein). Hence the individual dosage forms of each of the antibacterial drugs can be administered as separate forms (e.g. as separate tablets or capsules) as described herein or, in an alternative embodiment, may be administered as a single form containing all actives or as two or more forms (e.g. where there are three antibacterial drugs, one containing any two and the other containing the remaining one).

There is also provided a process for preparing a pharmaceutical formulation as defined herein comprising bringing into association any one (or more, e.g. the two essential active ingredients and, optionally, further antibacterials as defined herein) of the active ingredients of the combination of the invention, with one (or more) pharmaceutically acceptable excipient or carrier.

There is also provided a process for preparing a combination product as defined herein comprising:

- bringing into association each of the components (e.g. as separate pharmaceutical formulations) of the combination product and co-packaging (e.g. as a kit of parts) or indicated that the intended use is in combination (with the other components); and/or
- bringing into association each of the components in the preparation of a pharmaceutical formulation comprising such components.

General Preparation

The compounds according to the invention can generally be prepared by a succession of steps, each of which may be known to the skilled person or described herein.

Experimental Part

Q203 may be prepared in accordance with the methods described in the documents mentioned hereinbefore, e.g. patent document WO 2011/113606 and/or journal articles *J. Medicinal Chemistry*, 2014, 57 (12), pp 5293-5305 or *Nature Medicine*, 19, 1157-1160 (2013) by Pethe et al "Discovery of Q203, a potent clinical candidate for the treatment of tuberculosis". For example, in WO 2011/113606, compound (289) at page 126 provides characterising data for Q203, and preparation methods are described at pages 17-30, in *Nature Medicine*, the synthesis of the compound is described in the accompanying "Online Methods" as well as in the *J. Medicinal Chemistry* article in the experimental sections.

Other inhibitors of cytochrome $bc_1$ activity, may be those disclosed (and prepared using methods disclosed) in international patent applications WO 2017/001660 and WO 2017/001661, both of which are hereby incorporated by reference.

Compound X—this is Compound 28, as described in WO 2017/001660, and prepared according to the procedures described therein.

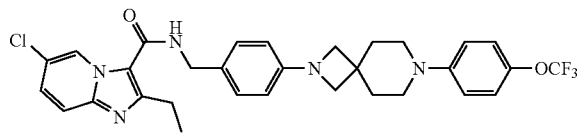 [SMILES: CCc1nc2ccc(Cl)cn2c1C(=O)NCc1ccc(N2CC3(CCN(c4ccc(OC(F)(F)F)cc4)CC3)C2)cc1]

Synthesis of Compound X

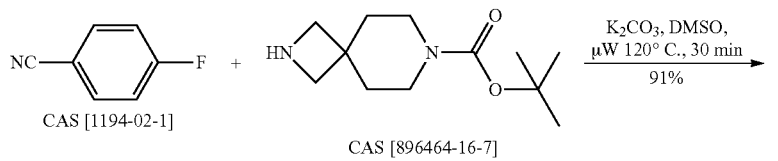

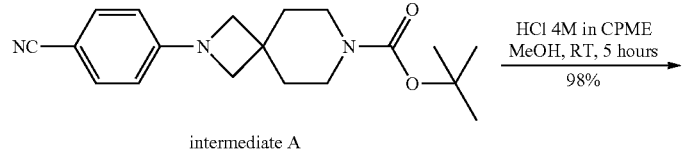

intermediate A

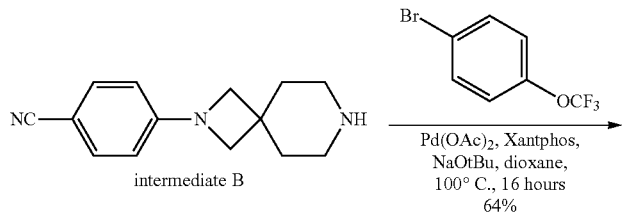

intermediate B

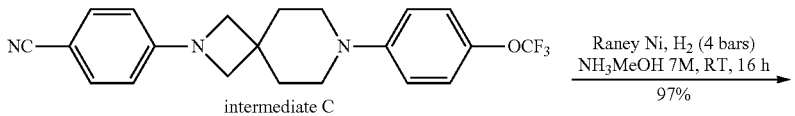

intermediate C

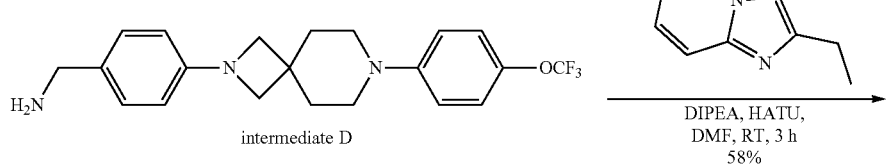

intermediate D

-continued

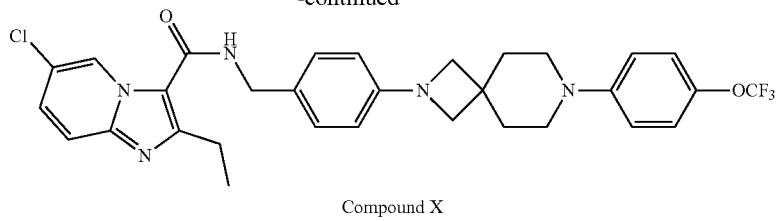

Compound X

Preparation of Intermediate A

A suspension of tert-butyl-2,7-diazaspiro[3.5]nonane-7-carboxylate (CAS [896464-16-7], 2.6 g, 11.49 mmol), 4-Fluorobenzonitrile (CAS [1194-02-1], 2.78 g, 22.98 mmol) and potassium carbonate (7.94 g, 57.44 mmol) in DMSO (40 mL) was heated at 120° C. using a single mode microwave (Biotage Initiator60) with a power output ranging from 0 to 400 W for 30 min [fixed hold time]. The mixture was diluted in EtOAc, washed with water (3×), brine (3×), dried over $MgSO_4$, filtered off and evaporated. The crude product was purified by preparative LC (irregular silica, 15-40 μm, 24 g, Grace, liquid loading, mobile phase gradient: Heptane/EtOAc from 90/10 to 80/20). The fractions containing product were combined and the solvent was removed in vacuo to give 2.9 g of intermediate A as a white solid (77%).

Preparation of Intermediate B

HCl 3M in CPME (22.1 mL, 88.6 mmol) was added to a solution of intermediate A (2.9 g, 8.86 mmol) in methanol (50 mL) at 0° C. The resulting mixture was allowed to warm to room temperature and stirred for 5 hours. The solution was evaporated, the residue was azeotroped with MeOH (twice) to give 4.22 g of crude compound. The crude was purified by preparative LC (irregular SiOH, 15-40 μm, 40 g, Grace, dry loading (silica), mobile phase gradient: from DCM/MeOH/aqNH3 100/0/0 to 90/10/1). The fractions containing product were combined and the solvent was removed in vacuo to give 1.25 g of intermediate B, as a white solid (62%).

Preparation of Intermediate C

In a Schlenck, a mixture of intermediate B (1 g, 4.40 mmol), 4-bromotrifluoromethoxybenzene (CAS [407-14-7], 0.981 mL, 6.60 mmol) and sodium t-butoxide (1.69 g, 17.6 mmol) in 1,4-dioxane (70 mL) was degassed by $N_2$ bubbling for 10 min before the addition of palladium acetate (0.099 g, 0.44 mmol) and Xantphos (0.255 g, 0.44 mmol). The resulting mixture was stirred at 100° C. overnight, then cooled to room temperature and filtered through a pad of Celite®. The cake was washed with EtOAc and the filtrate was evaporated to dryness. The residue was solubilized in EtOAc and washed with brine (2×). The organic layer was dried over $MgSO_4$, filtered and concentrated to dryness. The crude product was purified by preparative LC (Regular SiOH 15-40 μm, 24 g Grace, dry loading (SiOH), mobile phase gradient: from Heptane/EtOAc 95:5 to 70:30). The fractions containing product were combined and the solvent was removed in vacuo to give to give 1.07 g of intermediate C as an off-white solid (63%).

Preparation of intermediate D

In an autoclave, to a solution of intermediate C (3.73 g, 9.63 mmol) in ammonia 7N in MeOH (70 mL) was added Raney Nickel (2.45 g, 41.8 mmol) and the mixture was stirred at room temperature under 3 bar of H2 for 3 hours. The mixture was taken-up in EtOAc and filtered on a pad of Celite®, washed with EtOAc. The filtrate was evaporated in vacuo to give 3.68 g of intermediate D as an off-white solid (87%), used as such for next step.

Preparation of Compound X

Diisopropylethylamine (1.74 mL, 10.2 mmol) and HATU (1.94 g, 5.10 mmol) were added successively to a solution of 6-chloro-2-ethylimidazo[1,2-a]pyridine-3-carboxylic acid (CAS [1216142-18-5], 0.8 g, 3.40 mmol) in DMF (40 mL). The resulting mixture was stirred at room temperature for 20 min., then a solution of intermediate D (1.47 g, 3.74 mmol) in DMF (1 mL) was added and the mixture was stirred at room temperature for 2 days. EtOAc, brine, an aqueous solution of $NaHCO_3$ and water were added, the aqueous layer was extracted with EtOAc (twice). The combined organic layers were washed with water/brine (ratio 1/9; 4 times), dried over $MgSO_4$, filtered and concentrated to give the crude compound. The residue was purified by preparative LC (Irregular SiOH, 15-40 μm, 80 g Grace, dry loading (on SiOH), mobile phase gradient: from Heptane/EtOAc: 70/30 to 20/80). The fractions containing product were combined and the solvent was removed in vacuo to give 1.50 g as beige solid. This solid was coevaporated with EtOH (4 times), triturated in EtOH, filtered off and washed with EtOH (3 times) to give 1.18 g as a white solid. It was dried under high vacuum at 50° C. for 5 hours to give 1.17 g of Compound X as a white solid (58%).

$^1$H NMR (500 MHz, DMSO-d6) δ ppm 9.06 (d, J=1.3 Hz, 1H) 8.39 (t, J=5.8 Hz, 1H) 7.66 (d, J=9.5 Hz, 1H) 7.45 (dd, J=9.5, 2.2 Hz, 1H) 7.19 (br d, J=8.5 Hz, 2H) 7.17 (br d, J=8.8 Hz, 2H) 7.02 (d, J=8 Hz, 2H) 6.42 (d, J=8.5 Hz, 2H) 4.41 (d, J=5.8 Hz, 2H) 3.57 (s, 4H) 3.17-3.19 (m, 4H) 2.96 (q, J=7.5 Hz, 2H) 1.79-1.89 (m, 4H) 1.25 (t, J=7.5 Hz, 3H)

Melting point: 182.77° C./−65.98 J/g (DSC: 25° C. to 350° C./10° C. min/40 μl Al)

LC-MS: RT: 3.84, UV Area %: 98.23, MW: 597.20, BPM1: 598.6, BPM2: 596.4

Compound Y

This compound Y was prepared in accordance with the procedures described in international patent application WO 2017/001660 (see Compound 72):

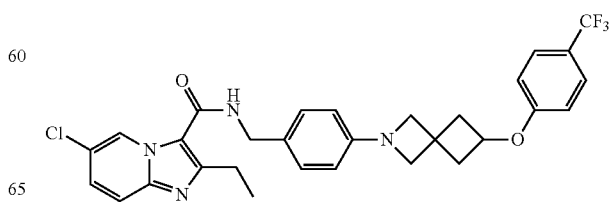

Synthesis of Compound Y

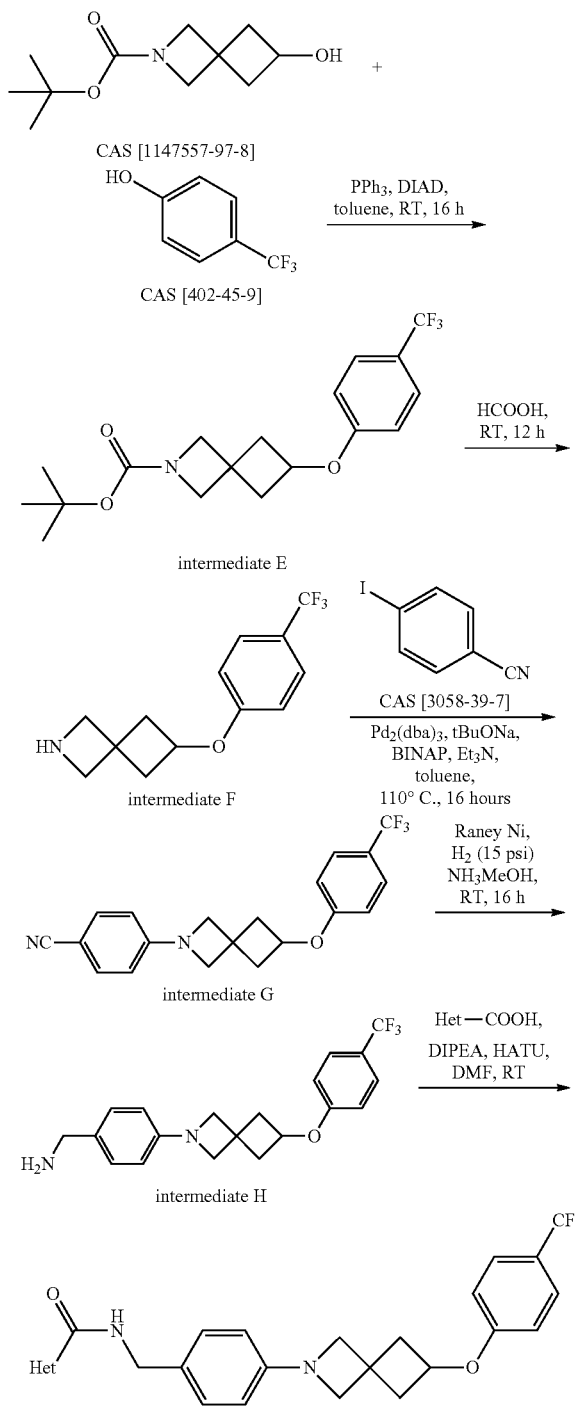

Preparation of intermediate E

DIAD (1.40 g, 6.92 mmol) in toluene (10 mL) was added to a solution of ten-butyl 6-hydroxy-2-azaspiro[3.3]heptane-2-carboxylate (CAS [1147557-97-8], 1.2 g, 5.63 mmol), 4-(trifluoromethyl)phenol (CAS [402-45-9], 1.10 g, 6.75 mmol), and triphenylphosphine (2.31 g, 8.80 mmol) in toluene (40 mL) at 0° C. under $N_2$ flow. The mixture was stirred overnight at room temperature. The mixture was concentrated. The crude product was purified by column chromatography over silica gel (petroleum ether/ethyl acetate from 1/0 to 3/1). The desired fraction was collected and concentrated to give intermediate E, 2 g, 99%.

Preparation of intermediate F

A mixture of intermediate E (2 g, 5.60 mmol) in formic acid (10 mL) was stirred for 12 hours. The mixture was concentrated to give intermediate F, 1.4 g, 97%.

Preparation of Intermediate G

A solution of intermediate F (1.4 g, 5.44 mmol), 4-iodobenzonitrile (CAS [3058-39-7], 0.99 g, 5.44 mmol), BINAP (0.203 g, 0.33 mmol), $Pd_2(dba)_3$ (0.1 g, 0.11 mmol), sodium tert-butoxide (1.57 g, 16.33 mmol) and triethylamine (0.38 mL) in toluene (50 mL) was stirred overnight at 110° C. under $N_2$ flow. The mixture was concentrated. The residue was dissolved in $CH_2Cl_2$ (100 mL) and water (100 mL). The organic layer was washed with brine (100 mL), dried over $MgSO_4$ and filtered. The filtrate was concentrated. The crude product was purified by column chromatography over silica gel (ethyl acetate/petroleum ether from 0 to 1/5). The desired fractions were collected and concentrated to give intermediate G, 1.8 g, 92%.

Preparation of Intermediate H

A mixture of intermediate G (0.2 g, 0.56 mmol) in ammonia 7N in methanol (20 mL) was hydrogenated with Raney Nickel (20 mg) as catalyst at 25° C. (15 Psi) for 16 hours. After uptake of $H_2$, the catalyst was filtered off and the filtrate was concentrated to give intermediate H, 0.2 g, 99%.

Preparation of Compound Y

Accordingly, Compound Y was prepared starting from 6-chloro-2-ethylimidazo[3,2-a]pyridine-3-carboxylic acid. CAS [1216142-18-5] and intermediate H (which coupling reaction may be performed under standard conditions, e.g. in a DMF solution of the carboxylic acid, HATU and diisopropylamine, the intermediate H may be added, stirred for 2 hours at room temperature, and the resultant product may be isolated/purified using standard methods) affording 0.035 g, 28%. 1H NMR (400 MHz, $CDCl_3$) δ ppm 9.52 (s, 1H) 7.53 (d, J=8.38 Hz, 3H) 7.29 (dd, J=9.48, 1.98 Hz, 1H) 7.23 (d, J=8.38 Hz, 2H) 6.86 (d, J=8.82 Hz, 2H) 6.46 (d, J=8.38 Hz, 2H) 5.99 (br. s., 1H) 4.64-4.70 (m, 1H) 4.58 (d, J=5.29 Hz, 2H) 3.95 (s, 2H) 3.90 (s, 2H) 2.94 (q, J=7.50 Hz, 2H) 2.80 (ddd, J=10.47, 6.95, 2.87 Hz, 2H) 2.43 (ddd, J=10.25, 6.73, 3.31 Hz, 2H) 1.38 (t, J=7.50 Hz, 3H)

Pyrazinamide (PZA) is an old drug that is therefore also widely available.

Pharmacological Examples

MIC Determination for Testing Compounds Against M. tuberculosis

Test 1

Appropriate solutions of experimental and reference compounds are made in 96 well plates with 7H9 medium. Samples of Mycobacterium tuberculosis strain H37Rv are taken from cultures in logarithmic growth phase. These are first diluted to obtain an optical density of 0.3 at 600 nm wavelength and then diluted 1/100, resulting in an inoculum of approximately 5×10 exp5 colony forming units per well. Plates are incubated at 37° C. in plastic bags to prevent evaporation. After 7 days, resazurin is added to all wells. Two days later, fluorescence is measured on a Gemini EM Microplate Reader with 543 excitation and 590 nm emission wavelengths and $MIC_{50}$ and/or $pIC_{50}$ values (or the like, e.g. $IC_{50}$, $IC_{90}$, $pIC_{90}$, etc) are (or were) calculated.

Test 2

Round-bottom, sterile 96-well plastic microtiter plates are filled with 100 µl of Middlebrook (1×) 7H9 broth medium. Subsequently, an extra 100 µl medium is added to column 2. Stock solutions (200× final test concentration) of compounds are added in 2 µl volumes to a series of duplicate wells in column 2 so as to allow evaluation of their effects on bacterial growth. Serial 2-fold dilutions are made directly in the microtiter plates from column 2 to 11 using a multipipette. Pipette tips are changed after every 3 dilutions to minimize pipetting errors with high hydrophobic compounds. Untreated control samples with (column 1) and without (column 12) inoculum are included in each microtiter plate. Approximately 10000 CFU per well of Mycobacterium tuberculosis (strain H37RV), in a volume of 100 µl in Middlebrook (1×) 7H9 broth medium, is added to the rows A to H, except column 12. The same volume of broth medium without inoculum is added to column 12 in row A to H. The cultures are incubated at 37° C. for 7 days in a humidified atmosphere (incubator with open air valve and continuous ventilation). On day 7 the bacterial growth is checked visually.

The 90% minimal inhibitory concentration ($MIC_{90}$) is determined as the concentration with no visual bacterial growth.

Test 3: Time Kill Assays

Bactericidal or bacteriostatic activity of the compounds can be determined in a time kill assay using the broth dilution method. In a time kill assay on Mycobacterium tuberculosis (strain H37RV), the starting inoculum of M. tuberculosis is $10^6$ CFU/ml in Middlebrook (1×) 7H9 broth. The antibacterial compounds are used at the concentration of 0.1 to 10 times the $MIC_{90}$. Tubes receiving no antibacterial agent constitute the culture growth control. The tubes containing the microorganism and the test compounds are incubated at 37° C. After 0, 1, 4, 7, 14 and 21 days of incubation samples are removed for determination of viable counts by serial dilution ($10^{-1}$ to $10^{-6}$) in Middlebrook 7H9 medium and plating (100 µl) on Middlebrook 7H11 agar. The plates are incubated at 37° C. for 21 days and the number of colonies are determined. Killing curves can be constructed by plotting the $log_{10}$ CFU per ml versus time. A bactericidal effect is commonly defined as 3-$log_{10}$ decrease in number of CFU per ml as compared to untreated inoculum. The potential carryover effect of the drugs is removed by serial dilutions and counting the colonies at highest dilution used for plating.

Test 4 (See Also Test 1 Above; in this Test a Different Strain of Mycobacterium tuberculosis Strain is Employed)

Appropriate solutions of experimental and reference compounds are made in 96 well plates with 7H9 medium. Samples of Mycobacterium tuberculosis strain EH 4.0 (361.269) are taken from cultures in stationary growth phase. These are first diluted to obtain an optical density of 0.3 at 600 nm wavelength and then diluted 1/100, resulting in an inoculum of approximately 5×10 exp5 colony forming units per well. Plates are incubated at 37° C. in plastic bags to prevent evaporation. After 7 days, resazurin is added to all wells. Two days later, fluorescence is measured on a Gemini EM Microplate Reader with 543 nm excitation and 590 nm emission wavelengths and $MIC_{50}$ and/or $pIC_{50}$ values (or the like, e.g. $IC_{50}$, $IC_{90}$, $pIC_{90}$, etc) are (or were) calculated. $pIC_{50}$ values may be recorded below in µg/mL.

Results

Compounds may be/are tested in Test 1, 2, 3 and/or 4 described above (in section "Pharmacological Examples").

Biological Example—Combinations

Protocol
The compounds employed were as follows:
Bedaquiline—"BDQ"
The following "$bc_1$ inhibitors": —Q203-Cpd "X" (see experimental)
Pyrazinamide (PZA)
Design of the Study
There were 14 study groups and 6 mice per group

| Study Group | Treatment (compound/dose in mg/kg) | Formulation concentration |
|---|---|---|
| 1 | BDQ 3 mg/kg | 0.3 mg/ml |
| 2 | Q203 20 mg/kg | 2.0 mg/ml |
| 3 | Cpd X 20 mg/kg | 2.0 mg/ml |
| 4 | PZA 150 mg/kg | 15 mg/ml |
| 5 | BDQ 3 mg/kg + PZA 150 mg/kg | 0.3 mg/ml + 15 mg/ml |
| 6 | Q203 20 mg/kg + PZA 150 mg/kg | 2 mg/ml + 15 mg/ml |
| 7 | Cpd X 20 mg/kg + PZA 150 mg/kg | 2 mg/ml + 15 mg/ml |
| 8 | BDQ 3 mg/kg + Q203 20 mg/kg | 0.3 mg/ml + 2 mg/ml |
| 9 | BDQ 3 mg/kg + Cpd X 20 mg/kg | 0.3 mg/ml + 2 mg/ml |
| 10 | BDQ 3 mg/kg + Q203 20 mg/kg + PZA 150 mg/kg | 0.3 mg/ml + 2 mg/ml + 150 mg/ml |
| 11 | BDQ 3 mg/kg + Cpd X 20 mg/kg + PZA 150 mg/kg | 0.3 mg/ml + 2 mg/ml + 150 mg/ml |
| 12 | Control C1 (day 1) | |
| 13 | Control C2 (day 12) | |
| 14 | Control C3 (day 41) | |

Generally, as can be seen from the table above the following doses of the relevant compounds and formulation concentrations were given:
bedaquiline (BDQ)—administered at a dose of 3 mg/kg; the formulation concentration being 0.3 mg/ml
the "$bc_1$ inhibitor" either Q203 or Cpd X—each administered at a dose of 3 mg/kg; the formulation concentration being 2 mg/ml
pyrazinamide (PZA)—administered at a dose of 150 mg/kg; the formulation concentration being 150 mg/ml
Methods
All treatments were evaluated on the lab strain H37Rv.
All formulations prepared in 20% HP-β-CD, and used for 5 treatments (one week).
For every dosing week a new formulation was prepared.
All formulations were solutions and stored at 4° C. during the study.

Stability of BDQ and Q203 in formulation was previously tested, for PZA and Cpd X the stability was tested after one week and found acceptable for both compounds Time Schedule, after mice were infected

| Necropsy Control 1 | Day 1 |
|---|---|
| Necropsy Control 2 | Day 12 |
| Start Treatment (for non-control groups) | Day 12 |
| Last treatment (for non-control groups) | Day 37 |
| Necropsy Control 3 | Day 41 |
| Necropsy Treatment Groups | Day 41 |

The mice were infected with *Mycobacterium tuberculosis* strain.

The drug sensitive H37Rv strain of MTB (stock 8) was thawed at ambient temperature and diluted 13 times in PBS for mouse inoculation. When 0.2 mL of this dilution is injected, each mouse receives $10^6$ bacteria.

90 (6 extra) Female 5-weeks old outbred Swiss mice, Charles River, were inoculated intravenously in the tail vein with 0.2 ml of a bacterial suspension containing±$10^6$ colony forming units (CFU)

Remark: since no mice died during the 12-day infection phase, the 6 remaining mice were used as "Necropsy Control 3" (at day 41).

Dosing (for Non-Control Groups)

The start of dosing was at Day 12

All groups are weighed once/week and the mean body weight/group is used to calculate the dose volume.

All mice were dosed orally with 10 ml/kg of the appropriate formulation, except the control groups, which were not treated.

All groups were treated once daily (on working days) for 4 consecutive weeks (hence, 5 times/week, 20 doses/treatments in total).

The last doses/treatments were given on Day 37.

Necropsy

At day 1 after the infection, 6 control mice were sacrificed and the lung and spleen were collected and deepfrozen at −80° C.

At day 12 after the infection, 6 control mice were sacrificed and the lung and spleen were collected and deepfrozen at −80° C.

At day 41, all control and treated animals are sacrificed, the lung and spleen were collected and deepfrozen at −80° C.

All spleens were weighed, and stored in cryo vials at −80° as a back-up organ.

All lungs were collected in homogenisation tubes.

Assessment of Infection and Treatment

The severity of infection and the effectiveness of treatments was assessed by counting the numbers of colony-forming-units (CFU) in the lungs.

Lungs were thawed and 2.5 ml PBS (+Ca/Mg) was added to each tube.

Lungs were homogenized and five 10-fold serial dilutions were made in PBS (+Ca/Mg), 111 µl homogenate+1 ml PBS.

From each individual lung, 200 µl of the undiluted suspension and five serial 10-fold dilutions, were plated on 7H11 agar plates (6-well) containing a mixture of antibiotics and antifungal to prevent contaminations.

CFU's were counted after incubation at 37° C. for 3 weeks.

The bactericidal effect of the treatment was defined as a significant decrease of the mean number of CFU in the treated group compared to pre-treatment value.

Preparation of Media

7H11 agar+0.4% charcoal+antibiotics
dissolve 8.4 g Middlebrook 7H11 agar (BD 283810) in 360 ml Aqua dest. containing 2.0 ml glycerol (AnalaR NORMAPUR, 24388.295)
add 0.4% or 1.6 g activated charcoal (SIGMA C9157)
autoclave at 121° C. for 15 min and cool to 55° C.
add 40 ml Middlebrook OADC Enrichment (BD 211886)
keep at 55° C.
Add antibiotics
   Amphotericin B: add 4.0 ml of stock of 10 mg/ml in water (=100 µg/ml final)
   Polymyxin B: add 0.4 ml of stock of 25 mg/ml in water (=25 µg/ml final)
   Carbenecillin: add 0.4 ml of stock of 50 mg/ml in water (=50 µg/ml final)
   Trimethoprim: add 0.4 ml of stock of 20 mg/ml in DMSO (=20 µg/ml final)
pipette 4 ml agar solution/6-well
allow to coagulate for 45 minutes in the Laminar Air Flow (with cover half-open)
store at 4° C. until ready to use (for maximum 1 month)

Results

| Study Group | Treatment (compound/dose in mg/kg) | mean log10 | Standard Deviation |
|---|---|---|---|
| 1 | BDQ 3 mg/kg | 4.46 | 0.49 |
| 2 | Q203 20 mg/kg | 4.55 | 0.08 |
| 3 | Cpd X 20 mg/kg | 4.75 | 0.22 |
| 4 | PZA 150 mg/kg | 3.47 | 0.45 |
| 5 | BDQ 3 mg/kg + PZA 150 mg/kg | 1.46 | 0.28 |
| 6 | Q203 20 mg/kg + PZA 150 mg/kg | 1.18 | 0.19 |
| 7 | Cpd X 20 mg/kg + PZA 150 mg/kg | 1.20 | 0.25 |
| 8 | BDQ 3 mg/kg + Q203 20 mg/kg | 4.29 | 0.25 |
| 9 | BDQ 3 mg/kg + Cpd X 20 mg/kg | 4.24 | 0.20 |
| 10 | BDQ 3 mg/kg + Q203 20 mg/kg + PZA 150 mg/kg | 1.10 | 0.00 |
| 11 | BDQ 3 mg/kg + Cpd X 20 mg/kg + PZA 150 mg/kg | 1.10 | 0.00 |
| 12 | Control C1 (day 1) | 4.82 | 0.51 |
| 13 | Control C2 (day 12) | 5.68 | 0.34 |
| 14 | Control C3 (day 41) | 6.00 | 0.48 |

The results above can be seen with reference to FIG. 1, which shows each the mean log 10 value for CFUs of each of the 14 study groups. It also shows a "cut off" value of 1.10, which is essentially the value at which the CFUs (or the bacterial infection) is so low that it cannot accurately be measured, or the CFUs are below the detectable level.

It can be seen that, compared to the control groups:
administering single agents (either bedaquiline alone, a $bc_1$ inhibitor alone, or pyrazinamide alone) resulted in mean log 10 CFUs that were still relatively high, with pyrazinamide having the best effects causing drop to a mean log 10 of 3.47
"double" combinations of bedaquiline with a $bc_1$ inhibitor resulted in a non-significant mean log 10 drop in CFUs (to 4.29 and 4.24)
"double" combinations with pyrazinamide gave a surprising reduction in CFUs, which is greater than a mere additive affect; "double" combinations with pyrazinamide show a synergistic effect as may be elucidated from the mean log 10 drop in CFUs; in particular, the "double" combination of pyrazinamide and a "$bc_1$ inhibitor" (either Q203 or Cpd X) gave the lowest mean log 10 values, out of all of the double combinations tested when the most synergistic double combinations (pyrazinamide+$bc_1$ inhibitor) were further combined with bedaquiline, these triple combinations effectively eliminated all detectable CFUs in the mice achieving the cut off values of 1.10

The invention claimed is:

1. A process for preparing a combination product, the process comprising bringing into association the following active ingredients:
   (i) Pyrazinamide (PZA), or a pharmaceutically acceptable salt thereof; and
   (ii) a cytochrome $bc_1$ inhibitor, or a pharmaceutically acceptable salt thereof.

2. The process as claimed in claim 1, wherein the cytochrome $bc_1$ inhibitor is Q203, or a pharmaceutically acceptable salt thereof.

3. The process as claimed in claim 1, further comprising bringing into association with active ingredients (i) and (ii) one or more additional antibacterial drugs.

4. The process as claimed in claim 3, wherein the one or more additional antibacterial drugs are anti-tuberculosis drugs selected from:
   agents known to interfere with the respiratory chain of *Mycobacterium tuberculosis*;
   antibacterial agents that target the electon transport chain;
   mycobacterial agents selected from rifampicin; isoniazid; pyrazinamide; amikacin;
   ethionamide; ethambutol; streptomycin; para-aminosalicylic acid; cycloserine;
   capreomycin; kanamycin; thioacetazone; PA-824; delamanid; quinolones;
   fluoroquinolones; macrolides; rifamycins; rifabutin; rifapentin; delanamid; pretonamid, or a combination thereof.

5. The process as claimed in claim 4, wherein the one or more additional antibacterial drugs comprise bedaquiline, clofazimine, or a combination thereof.

6. The process as claimed in claim 1, wherein the combination product further comprises a pharmaceutically acceptable excipient or diluent.

* * * * *